United States Patent
Nam-Koong (10) Patent No.: US 7,075,074 B2
(45) Date of Patent: Jul. 11, 2006

(54) ELECTRON BEAM INSPECTION APPARATUS AND METHOD FOR TESTING AN OPERATION STATE OF AN ELECTRON BEAM INSPECTION APPARATUS

(75) Inventor: Whan Nam-Koong, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 10/868,220

(22) Filed: Jun. 16, 2004

(65) Prior Publication Data
US 2004/0262519 A1    Dec. 30, 2004

(30) Foreign Application Priority Data
Jun. 26, 2003   (KR)  .................. 10-2003-0042241

(51) Int. Cl.
*G01N 23/00* (2006.01)
*G21K 7/00* (2006.01)
(52) U.S. Cl. ........................... 250/310; 250/307
(58) Field of Classification Search ............. 250/559.3, 250/307, 310
See application file for complete search history.

(56) References Cited

U.S. PATENT DOCUMENTS

| | | | |
|---|---|---|---|
| 5,835,227 A * | 11/1998 | Grodnensky et al. | 356/399 |
| 6,107,637 A * | 8/2000 | Watanabe et al. | 250/559.3 |
| 6,265,719 B1 | 7/2001 | Yamazaki et al. | 250/310 |
| 6,797,975 B1 * | 9/2004 | Nishiyama et al. | 250/559.04 |
| 6,822,259 B1 * | 11/2004 | Wang et al. | 257/48 |

FOREIGN PATENT DOCUMENTS

| | | |
|---|---|---|
| JP | 2001052981 | 2/2001 |
| KR | 1020020030674 A | 4/2002 |
| KR | 1020020046928 | 6/2002 |

* cited by examiner

*Primary Examiner*—John R. Lee
*Assistant Examiner*—Jennifer Yantomo
(74) *Attorney, Agent, or Firm*—Volentine Francos & Whitt, pllc (57) ABSTRACT

In a method for testing an operation state of an electron beam inspection apparatus, an electron beam sequentially scans a plurality of scan lines in a predetermined inspection area on a substrate. A detector detects secondary electrons emitted from the scan lines and an image acquisition unit acquires inspection images corresponding to the scan lines from the secondary electrons. An image processing unit analyzes the inspection images using an initial sensitivity in order to detect defects on the scan lines. A graphic unit produces an inspection graph indicating the number of defects and an operation unit compares the inspection graph with a reference graph. A compensator compensates a sensitivity difference corresponding to a difference between the inspection graph and the reference graph.

29 Claims, 10 Drawing Sheets

ELECTRON BEAM INSPECTION APPARATUS AND METHOD FOR TESTING AN OPERATION STATE OF AN ELECTRON BEAM INSPECTION APPARATUS

FIELD OF THE INVENTION

Embodiments of the present invention relate to an electron beam inspection apparatus. In embodiments, an electron beam inspection apparatus detects defects on a substrate using an electron beam and a method tests the operation state of the electron beam inspection apparatus.

The present application claims priority from Korean Patent Application No. 2003-42241, filed Jun. 26, 2003, the disclosure of which is incorporated herein by reference in its entirety.

DESCRIPTION OF THE RELATED ART

Semiconductor devices may be manufactured through a three-step process. In a first step, a fabrication process is performed for forming electronic circuits on a silicon wafer (i.e. a semiconductor substrate). In a second step, an electrical die sorting (EDS) process is performed for inspecting electrical characteristics of the semiconductor devices formed on the semiconductor substrate in the fabrication process. In a third step, a packaging process is performed for packaging the semiconductor devices in epoxy resins and individuating the semiconductor devices.

The fabrication process may include various unit processes. Examples of the unit processes are a deposition process, a photolithography process, an etching process, a chemical mechanical polishing process, an ion implantation process, a cleaning process, and an inspection process.

The inspection process may be performed to detect defects such as scratches, particles and residue remaining on the semiconductor substrate in a layer, or unintentional patterns formed on the semiconductor substrate. The defects deteriorate the performance of the semiconductor devices as well as lower production yield in manufacturing the semiconductor devices.

Various inspection apparatuses may be employed in the inspection process. Examples of various inspection apparatuses are secondary ion mass spectrometry using an ion beam, a surface inspection apparatus using a laser beam, and an inspection apparatus using an electron beam (e.g. scanning electron microscope, a transmission electron microscope, and an electron beam inspection apparatus).

U.S. Pat. No. 5,917,588 to Addiego discloses an automated specimen inspection system and a method of distinguishing features or anomalies under either bright field or dark field illumination. U.S. Pat. No. 6,215,551 to Nikoonahad et al. discloses a scanning system for inspecting anomalies on surfaces. The scanning system directs a focused beam of light at a grazing angle towards the surface to be inspected and detects the anomalies by collecting the light scattered form the surface of a wafer. U.S. Pat. No. 6,407,373 to Dotan discloses an apparatus and method for reviewing defects on an object using an optical microscope and a scanning electron microscope (SEM). U.S. Pat. No. 6,265,719 to Yamazaki et al. discloses an inspection method and apparatus using an electron beam.

The electron beam inspection apparatus may include an electron beam source, a stage, a driving unit, a detector, an image acquisition unit, an image processing unit, and a display unit. The electron beam source can generate an electron beam. The stage can support a substrate (e.g. a silicon wafer). The driving unit can adjust a position of the stage. The detector can detect secondary electrons emitted from a predetermined inspection area on the substrate. The image acquisition unit can acquire an inspection image from the detected secondary electrons. The image processing unit can analyze the inspection image to detect defects existing in the inspection area. The display unit can display the inspection image.

The electron beam source may include an electron gun for generating electrons and a column having a magnetic lens unit. The magnetic lens unit extracts the electrons to form the electron beam and controls an advancing direction of the electron beam. The electron gun includes a filament for emitting the electrons and an extraction electrode for extracting the electrons. The electrons extracted through the extraction electrode are irradiated onto the inspection area of the substrate through the magnetic lens unit. The magnetic lens unit includes a pair of condenser lenses for condensing the extracted electrons to form the electron beam and an objective lens for adjusting a spot size of the electron beam irradiated onto the inspection area of the substrate.

The electron beam formed by the condenser lens is deflected by a scan coil disposed between the pair of condenser lenses and the objective lens. The deflected electron beam scans the inspection area of the substrate through the objective lens. The intensity and spot size of the electron beam may be adjusted by an electric field strength and a magnetic field strength formed by the magnetic lens unit.

The electric field strength and the magnetic field strength may vary with time. Variations of the electric field strength and the magnetic field strength may cause a change in optical characteristics of an electron beam. As a result, a detection rate of defects may deteriorate.

A process for testing an operation state of the electron beam apparatus is periodically performed to prevent the detection rate of the defects from deteriorating. A reference substrate having a predetermined number of defects is used in the testing process for the electron beam inspection apparatus. The number of defects detected from the reference substrate by the electron beam inspection apparatus is compared with the predetermined number. When a difference between the number of the detected defects and the predetermined number exceeds a predetermined tolerance range, a sensitivity used in an image analysis step may be adjusted or the electric field strength and the magnetic field strength may be adjusted.

The inspection process on the reference substrate should be performed more than once in order to confirm that a normal defect detection rate has been restored after adjustment of the sensitivity, the electric field strength, and/or the magnetic field strength. However, it is difficult to successively perform the inspection process on the same reference substrate because of charging effects generated by irradiation of the electron beam. The time required for removing the charging effects of the reference substrate lowers throughput of the electron beam inspection apparatus. In addition, to confirm whether or not the sensitivity, the electric field strength, and/or the magnetic field strength has been correctly adjusted, the inspection process should be repeatedly performed from a few times to dozens of times.

An amount of the secondary electrons emitted along a plurality of scan lines or a plurality of scan swaths in the inspection area of the substrate may be varied in accordance with the plurality of scan lines. Thus, it is difficult to judge the operation state of the electron beam inspection apparatus from only the amount of the secondary electrons. It is necessary to repeatedly perform the electron beam inspection process on the reference substrate in order to ensure operational reliability of the electron beam inspection apparatus. Accordingly, during this recalibration, the time required for testing the operation state of the electron beam inspection apparatus may be increased and the throughput of the electron beam inspection apparatus may be decreased.

SUMMARY OF THE INVENTION

Embodiments of the present invention relate to a method for testing an operation state of an electron beam inspection apparatus using an inspection graph that indicates the number of defects existing on a substrate and a reference graph. Embodiments also provide an electron beam inspection apparatus for performing the testing method.

According to embodiments of the present invention, a method for testing the operation state of an electron beam inspection apparatus comprises sequentially scanning a plurality of scan lines in a predetermined inspection area on a substrate with an electron beam, detecting secondary electrons emitted from the scan lines, acquiring inspection images corresponding to the scan lines from the detected secondary electrons, analyzing the inspection images using an initial sensitivity to produce an inspection graph indicating the number of defects on the scan lines, and comparing the inspection graph with a reference graph.

The defects may be detected by comparing gray levels of pixels with one another, each pixel representing a part of the inspection images. The reference graph may be produced by analyzing experimental images acquired from a reference substrate using a reference sensitivity. The initial sensitivity may be substantially identical to the reference sensitivity. When the difference between the inspection graph and the reference graph exceeds a predetermined tolerance range, the initial sensitivity may be adjusted so that the difference is within the tolerance range.

The reference graph may be acquired by performing the following steps: Scanning a plurality of scan lines sequentially in a predetermined experimental area on a reference substrate using the electron beam. Detecting secondary electrons emitted from the scan lines in the experimental area. Acquiring experimental images from the detected secondary electrons in the experimental area. Analyzing the experimental images using an experimental sensitivity so as to produce an experimental graph indicating the number of defects on the scan lines in the experimental area. Repeatedly analyzing the experimental images while the experimental sensitivity is gradually increased or decreased. Selecting the reference graph from a plurality of experimental graphs produced by repeatedly analyzing the experimental images.

According to embodiments of the present invention, a step of comparing an inspection graph with a reference graph may be performed by comparing an inspection graph area with a reference graph area. Areas of the experimental graphs including the reference graph are calculated. The inspection graph area is calculated. The calculated inspection graph area is compared with the reference graph area referring to an area variation graph, showing an area variation of the experimental graphs. The initial sensitivity may be adjusted in accordance with a sensitivity difference corresponding to a difference in value between the inspection graph area and the reference graph area. The area variation graph may be expressed by a functional equation (e.g. a simple equation or a quadratic equation). The sensitivity difference may be obtained from the functional equation.

The electron beam inspection apparatus for performing the testing method may comprise an electron beam source, a stage, a driving unit, a detector, an image acquisition unit, an image processing unit, a graphic unit, and/or an operation unit. The electron beam source can generate an electron beam and control an advancing direction of the electron beam so that the electron beam scans a plurality of scan lines sequentially in a predetermined inspection area on a substrate. The stage can support the substrate. The driving unit can adjust a position of the stage such that the electron beam is irradiated onto a surface of the inspection area. The detector can detect secondary electrons emitted from the scan lines. The image acquisition unit, connected to the detector, can acquire a plurality of inspection images corresponding to the scan lines from the detected secondary electrons. The image processing unit can analyze the inspection images using an initial sensitivity in order to detect defects on the scan lines. The graphic unit can produce an inspection graph indicating the number of detected defects on the scan lines. The operation unit can compare the inspection graph with a reference graph.

The operation unit may include a first operator, a comparator, and a second operator. The first operator can calculate areas of the experimental graphs, a reference graph area, and an inspection graph area. The comparator can compare the inspection graph area with the reference graph area. The second operator can determine a sensitivity difference corresponding to a difference in value between the inspection graph area and the reference graph area.

The electron beam inspection apparatus may further include a compensator and a display unit. The compensator can compensate the initial sensitivity in accordance with the sensitivity difference corresponding to the difference in value between the inspection graph area and the reference graph area. The display unit can display the inspection graph, the reference graph and the experimental graphs.

According to embodiments of the present invention, the operation state of the electron beam inspection apparatus may be readily confirmed by comparing the inspection graph with the reference graph. The sensitivity of the electron beam inspection apparatus may be compensated in accordance with a comparison result between the graphs. Accordingly, there may be no need for repeated performance of the operation state testing process on the electron beam inspection apparatus. Further, in embodiments, the time required for performing the operation state testing process on the electron beam inspection apparatus may be decreased and the throughput of the electron beam inspection apparatus and the productivity of semiconductor devices may be improved.

DESCRIPTION OF THE PREFERRED EMBODIMENTS

Embodiments of the present invention are described more fully hereinafter with reference to the accompanying drawings. The invention may, however, be embodied in many different forms and should not be construed as limited to the embodiments set forth herein. Rather, these embodiments are provided so that this disclosure will be thorough and complete and will fully convey the scope of the invention to those skilled in the art.

Figure 1:
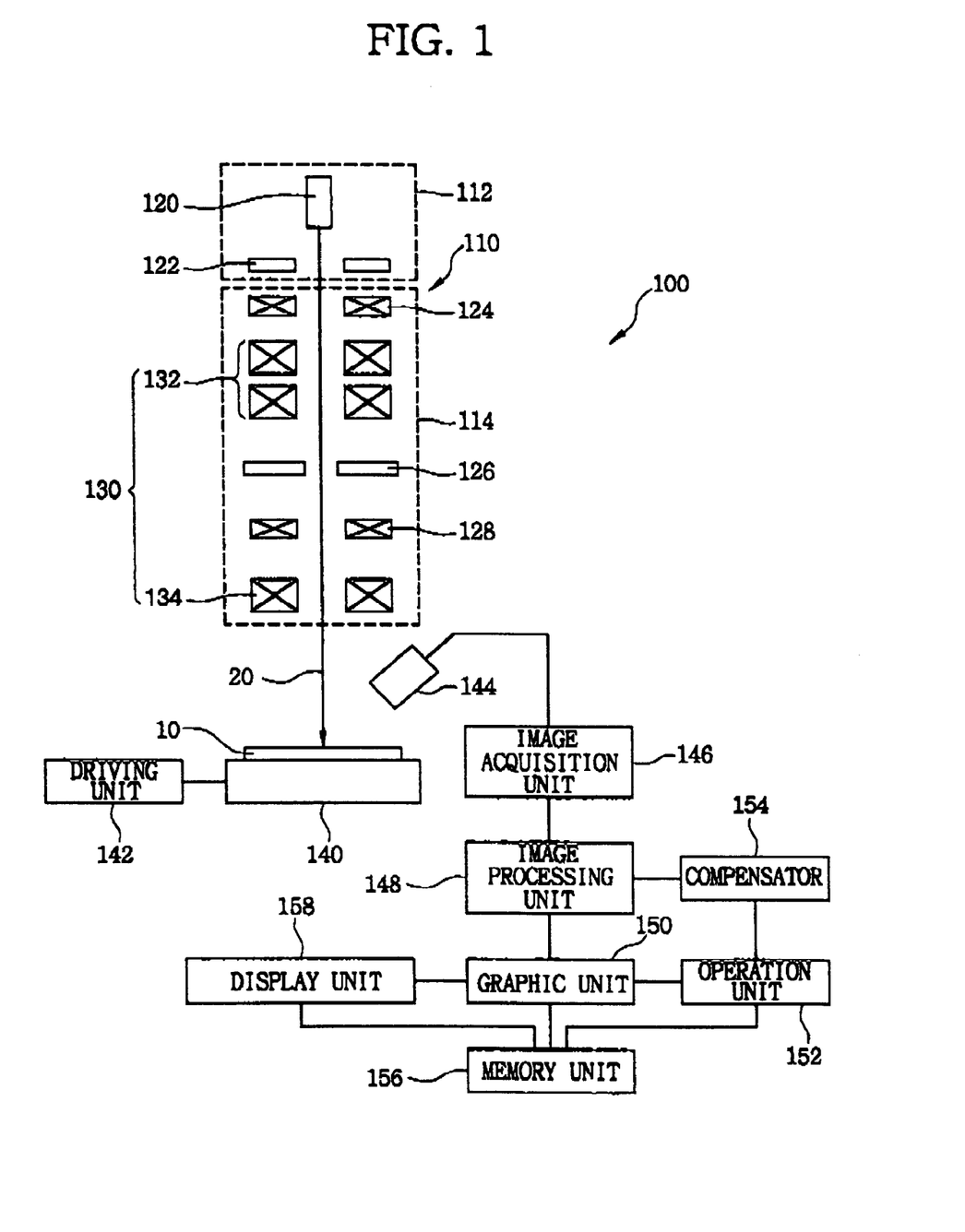
FIG. 1 is an example schematic view illustrating an electron beam inspection apparatus.
Figure 2:
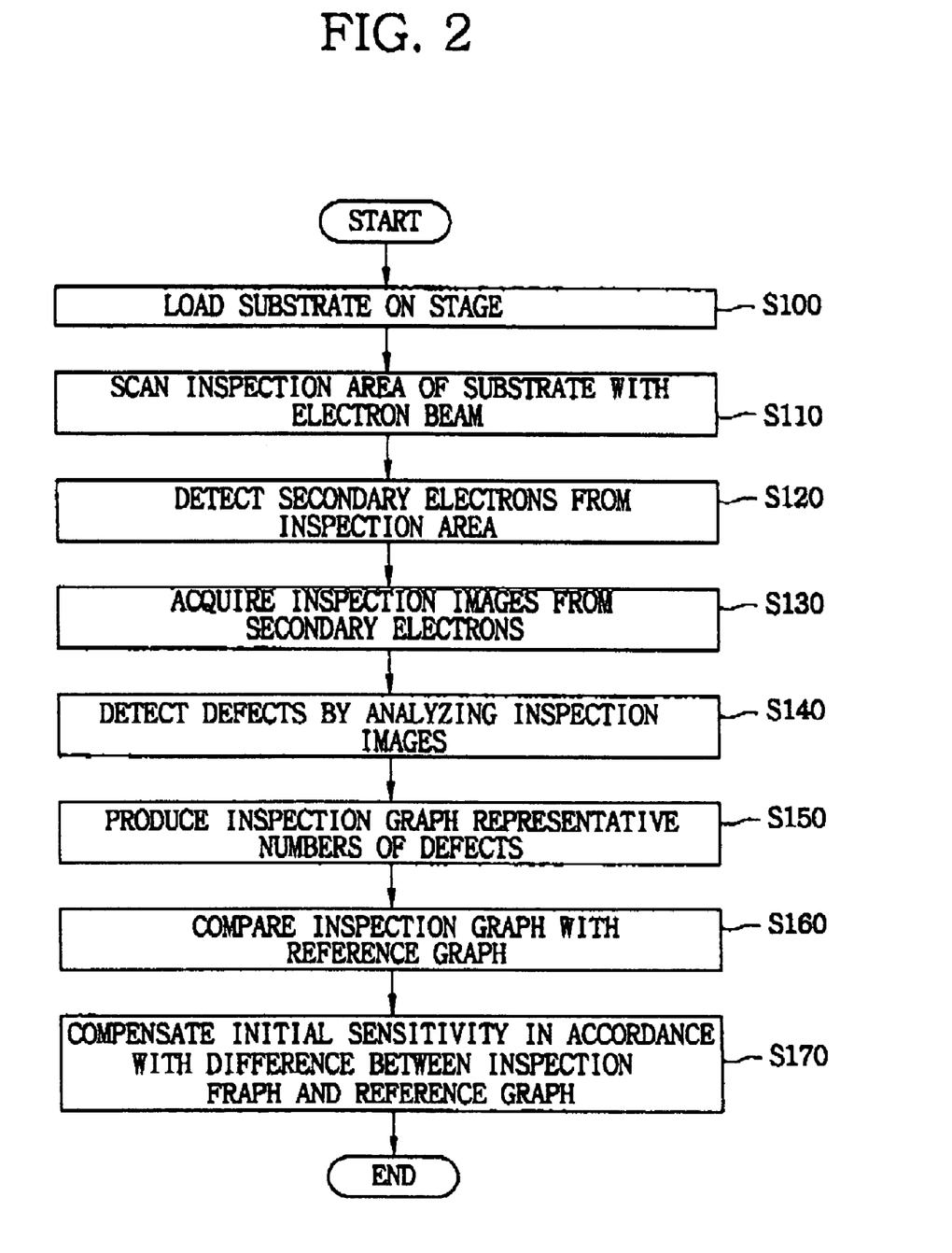
FIG. 2 is an example flow chart illustrating a method for testing an operation state of a electron beam inspection apparatus.

FIG. 1 is an example schematic view illustrating an electron beam inspection apparatus, according to embodiments of the present invention. FIG. 2 is an example flow chart illustrating a method for testing an operation state of the electron beam inspection apparatus illustrated in FIG. 1. An electron beam inspection apparatus 100 may include an electron beam source 110, a stage 140, a driving unit 142, a detector 144, an image acquisition unit 146, an image processing unit 148, a graphic unit 150, an operation unit 152, a compensator 154, a memory unit 156, and a display unit 158.

The electron beam source 110 may include an electron gun 112 and a column 114. The electron gun 112 can generate electrons. The column 114 can form the electrons into an electron beam 20 and irradiate the electron beam 20 onto a surface of a substrate 10 (e.g. a silicon wafer). The electron gun 112 may include a filament 120 that emits electrons and an extraction electrode 122 that extracts electrons. The column 114 may include an axis adjustment coil 124, a magnetic lens 130, an aperture 126, and/or a scan coil 128.

The magnetic lens 130 may be a cylindrical shaped electromagnet and may collect the electrons by forming an electric field and a magnetic field. The electron beam formed by the electron gun 112 may have a cross-sectional area of about 10 μm to about 50 μm and a spot size of the electron beam being irradiated onto the substrate 10 is about 5 nm to about 200 nm. The magnetic lens 130 may include a pair of condenser lenses 132 and an objective lens 134. The pair of condenser lenses 132 condenses the electron beam formed by the electron gun 112 and adjusts the intensity of the electron beam. The objective lens 134 may adjust the spot size and a focal length of the electron beam being irradiated onto the substrate 10.

The axis adjustment coil 124 may be disposed between the extraction electrode 122 and the magnetic lens 130 and may adjust an inclination of an axis of the electron beam formed by the extraction electrode 122 so that the electron beam is advanced along an optical axis of the magnetic lens 130. The aperture 126 and the scan coil 128 may be disposed between the condenser lenses 132 and the objective lens 134. The scan coil 128 may deflect the electron beam transmitted through the aperture 126 so that the electron beam scans the surface of the substrate 10.

The stage 140 supports the substrate 10. The driving unit 142 is connected to the stage 140 and adjusts a position of the stage 140 so that the electron beam 20 is irradiated onto a predetermined inspection area. The inspection area includes a plurality of scan lines at a predetermined position on the substrate 10. A Cartesian robot may be used as the driving unit 142. A second driving unit (not shown) for adjusting a height of the stage 140 may be connected to a lower portion of the stage 140. A piezoelectric element may be used as the second driving unit.

The detector 144 may detect secondary electrons emitted from the scan lines in the inspection area of the substrate 10 resulting from irradiation from the electron beam 20. The detector 144 may convert a current signal corresponding to the detected secondary electrons into a voltage signal and amplify the voltage signal. A bias voltage for collecting the secondary electrons may be applied to the detector 144.

The image acquisition unit 146 connected to the detector 144 may convert the amplified voltage signal into image data corresponding to the inspection area of the substrate 10. The image data may include gray levels of pixels, each pixel that is part of one of a plurality of inspection images corresponds to scan lines in the inspection area of the substrate 10. The image acquisition unit 146 may serve as an analog digital (AD) converter for converting an analog voltage signal into digital image data.

The image processing unit 148 connected to the image acquisition unit 146 may detect defects on the inspection area of the substrate 10 by analyzing the image data using an initial sensitivity. The image processing unit 148 may compare the gray levels of the pixels. Each of the pixels that are part of an inspection image are compared with one another to detect the defects on the inspection area. The plurality of scan lines may substantially cover the inspection area and the image processing unit 148 detects the number of defects corresponding to the scan lines.

The number of defects may be varied in accordance with the initial sensitivity. That is, when the initial sensitivity is set harder (lower) than a predetermined level, a total number of the defects detected on the inspection area may be higher than an actual number of defects. In contrast, when the initial sensitivity is set looser (higher) than the predetermined level, the total number of the defects detected on the inspection area may be lower than the actual number of the defects. Consequently, the total number of detected defects may be inversely proportional to the initial sensitivity.

If an electron beam inspection apparatus is calibrated correctly, the initial sensitivity is substantially identical to a reference sensitivity produced by repeatedly performing the inspection process on a reference substrate. The reference substrate may be manufactured by forming predetermined numbers of defects having predetermined positions.

The graphic unit 150 connected to the image processing unit 148 may produce an inspection graph showing the scan lines and the numbers of defects. The operation unit 152 may compare the inspection graph with a reference graph of the reference substrate using the reference sensitivity. The reference graph may be selected from a plurality of experimental graphs. The experimental graphs may be produced by repeatedly performing the inspection process in a predetermined experimental area on the reference substrate while an experimental sensitivity is gradually increased or decreased.

The detector 144 may detect secondary electrons emitted from the experimental area of the reference substrate which resulted from irradiation of the electron beam 20. Experimental images and an experimental graph are produced from the secondary electrons detected from the experimental area. A plurality of experimental graphs corresponding to a plurality of experimental sensitivities may be produced by repeatedly analyzing the experimental images while the experimental sensitivity is gradually increased or decreased. One of the experimental graphs corresponding to the actual number of defects of the experimental area may be selected for the reference graph. The reference sensitivity is an experimental sensitivity corresponding to the selected reference graph and the experimental graphs may be produced by the image processing unit 148 and the graphic unit 150.

The experimental images, the plurality of experimental graphs, the reference graph and the inspection graph may be stored in the memory unit 156, and may be displayed by the display unit 158. The operation unit 152 may compare the inspection graph with the reference graph. The operation unit 152 may include a first operator for calculating areas of the experimental graphs, a reference graph area and an inspection graph area. The operation unit 152 may include a comparator for comparing the inspection graph area with the reference graph area and a second operator for determining a sensitivity difference corresponding to a difference in value between the inspection graph area and the reference graph area. Result data that is produced by the operation unit 152 may be stored in the memory unit 156.

The compensator 154 may compensate the initial sensitivity in accordance with a difference between the inspection graph and the reference graph. The compensator 154 may compensate the initial sensitivity in accordance with the sensitivity difference corresponding to the difference in value between the inspection graph area and the reference graph area. Alternatively, the sensitivity difference may be produced using an area variation graph showing the area variation of the experimental graphs. The operation unit 152 may include a third operator for producing the area variation graph showing an area variation of the experimental graphs in accordance with a variable amount of the experimental sensitivity, a functional equation graph showing the area variation, and/or the sensitivity difference corresponding to the difference value between the inspection graph area and the reference graph area. The functional equation may be a simple equation or quadratic equation.

Figure 3:
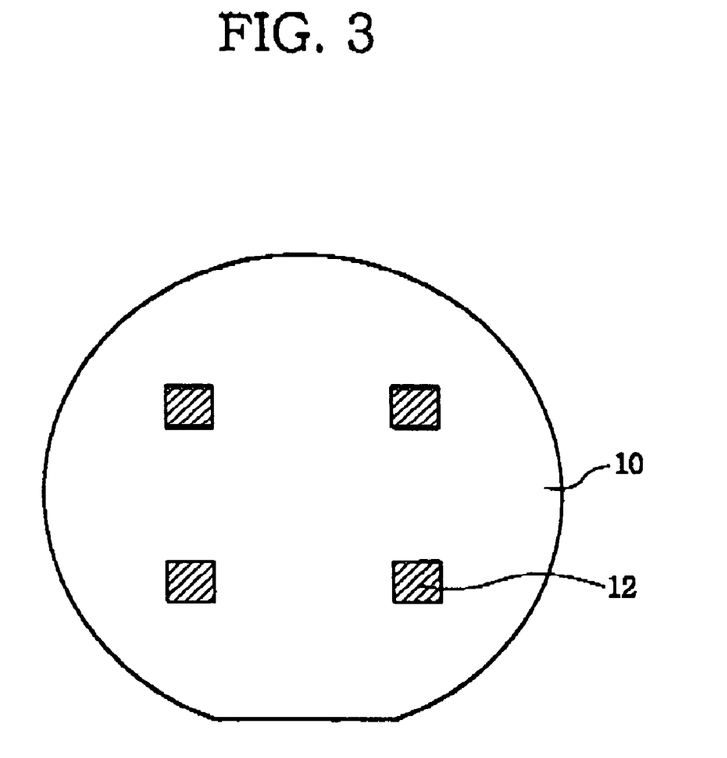
FIG. 3 is an example plan view showing a predetermined inspection area on a substrate.
Figure 4:
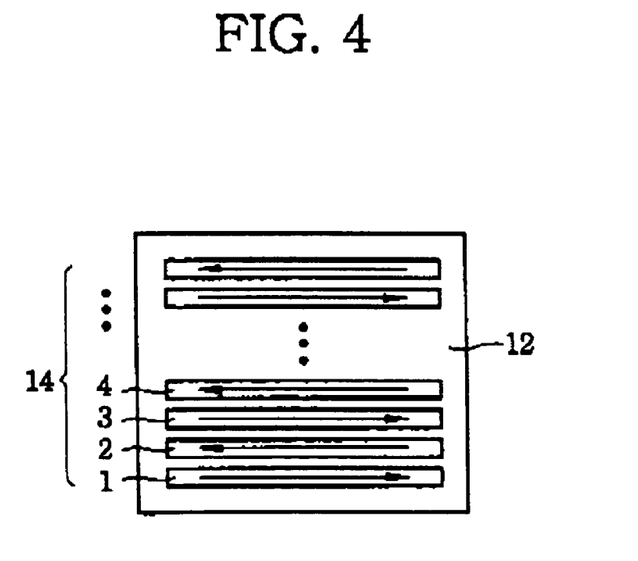
FIG. 4 is an example enlarged plan view of a inspection area.
Figure 5:
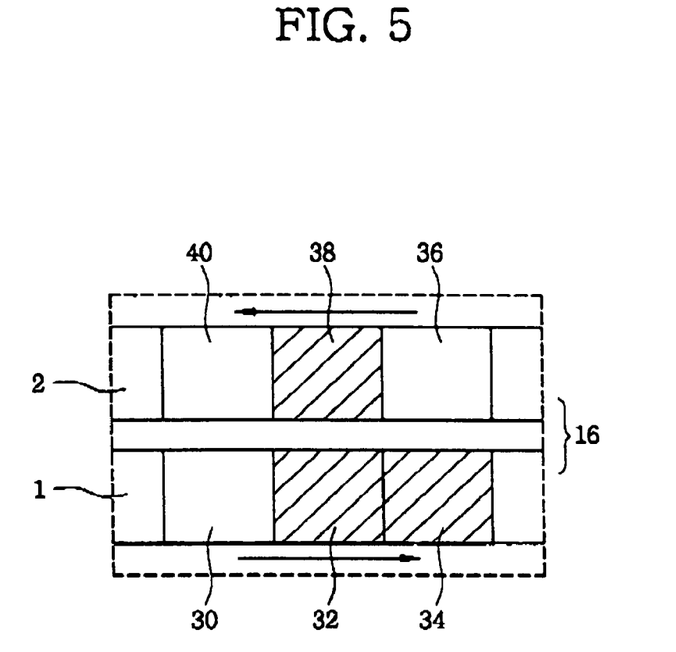
FIG. 5 is an example enlarged plan view of pixels in an inspection area.
Figure 6:
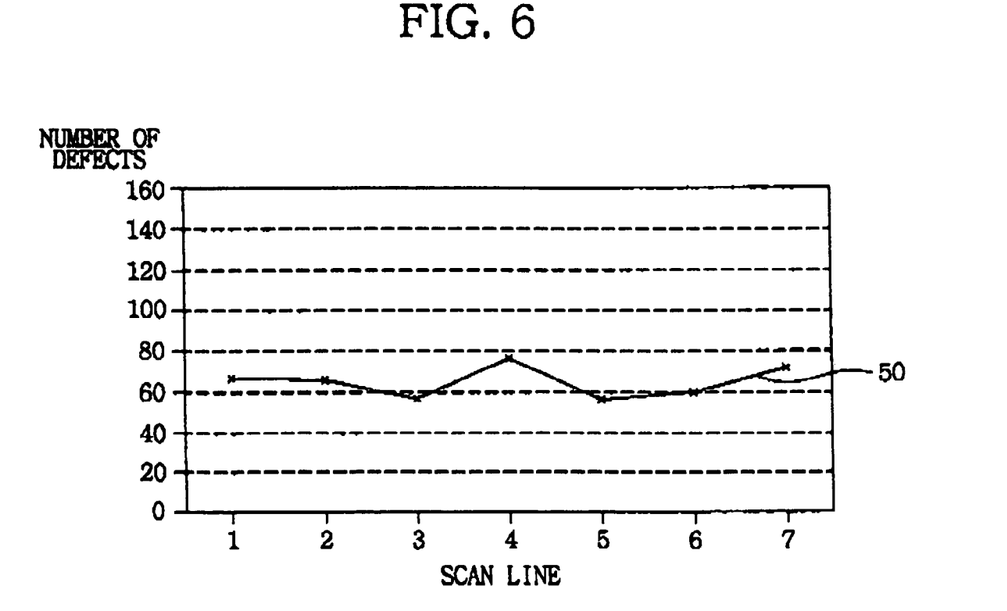
FIG. 6 is an example inspection graph indicating the number of defects detected in an inspection area.

FIG. 3 is an example plan view showing a predetermined inspection area on a substrate. FIG. 4 is an example enlarged plan view of the inspection area as shown in FIG. 3. FIG. 5 is an example enlarged plan view of pixels in the inspection area as shown in FIG. 4. FIG. 6 is an example inspection graph indicating the number of defects detected in the inspection area.

A method for testing an operation state of the electron beam inspection apparatus 100 is shown in FIGS. 1 and 2 will be described with reference to FIGS. 1 to 6. In step S100, the substrate 10 is loaded onto the stage 140. The driving unit 142 adjusts the position of the stage 140 such that the electron beam 20 is irradiated onto the predetermined inspection area 12 of the substrate 10 supported by the stage 140. The inspection area 12 may be arbitrarily set on the substrate 10 and includes the predetermined scan lines 14 substantially covering the entire surface thereof, as shown in FIGS. 3 and 4.

In step S110, the electron beam 20 scans the inspection area 12. The electron beam 20 generated from the electron beam source 110 scans the scan lines 14 sequentially in the inspection area 12 as shown in FIG. 4. In step S120, the secondary electrons emitted from the inspection area 12 are detected. The secondary electrons are emitted along the scan lines by means of the irradiation of the electron beam 20 and are detected by the detector 144 to which the bias voltage is applied. The detector 144 converts the current signal corresponding to detected secondary electrons into the voltage signal and amplifies the voltage signal.

In step S130, the inspection images 16 are then acquired from the secondary electrons. The voltage signal amplified by the detector 144 is converted into digital image data of the inspection images 16 corresponding to the scan lines 14 by the image acquisition unit 146.

In step S140, the defects are detected by analyzing the inspection images 16. The image processing unit 148 analyzes the inspection images 16 using the initial sensitivity, and then detects the defects on the inspection area 12 by scan lines 14. As shown in FIG. 5, a second pixel 32 has a different gray level from that of a first pixel 30 adjacent along a first scan line 1, and has a substantially identical gray level to that of a third pixel 34 opposite to the first pixel 30. A fifth pixel 38 has a different gray level from those of a fourth pixel 36 and a sixth pixel 40 adjacent along a second scan line 2. Here, the second pixel 32 and the fifth pixel 38 are detected as the defects. That is, a pixel having a different gray level from at least one of the adjacent pixels or a pixel having a different gray level from all adjacent pixels may be detected as the defects. In the figures, the depicted arrow indicates the scanning direction of the electron beam 20.

In step S150, the inspection graph 50 indicating the number of the defects produced. In FIG. 6, the graphic unit 150 produces the inspection graph 50 indicating the number of defects corresponding to the scan lines 14. In step S160, the inspection graph 50 is compared with the reference graph. The inspection graph 50 and the reference graph are displayed by the display unit 158 and may be compared by the naked eye.

In step S170, the initial sensitivity used in the inspection process is compensated in accordance with the difference between the inspection graph 50 and the reference graph. A worker (i.e. a user) may ascertain whether or not the difference between the inspection graph 50 and the reference graph is within a predetermined tolerance range. When the difference between the inspection graph 50 and the reference graph exceeds the tolerance range, the initial sensitivity may be adjusted so that the difference is within the tolerance range.

The reference graph may be acquired from the experimental area of the reference substrate and the method for testing the operation state of the electron beam inspection apparatus may also be performed using the reference substrate. In embodiments, the substrate 10 used in the testing method of the electron beam inspection apparatus is the reference substrate and the inspection area 12 is the experimental area. In some circumstances, the initial sensitivity may be substantially identical to the reference sensitivity.

When the difference between the inspection graph 50 and the reference graph exceeds the tolerance range, the operation state of the electron beam inspection apparatus may be judged to be abnormal, which may be due to variations of the electric field and the magnetic field. The variations of the electric field and the magnetic field may be compensated by adjusting the initial sensitivity. Consequently, the operation state of the electron beam inspection apparatus may be restored to a normal state.

Figure 7:
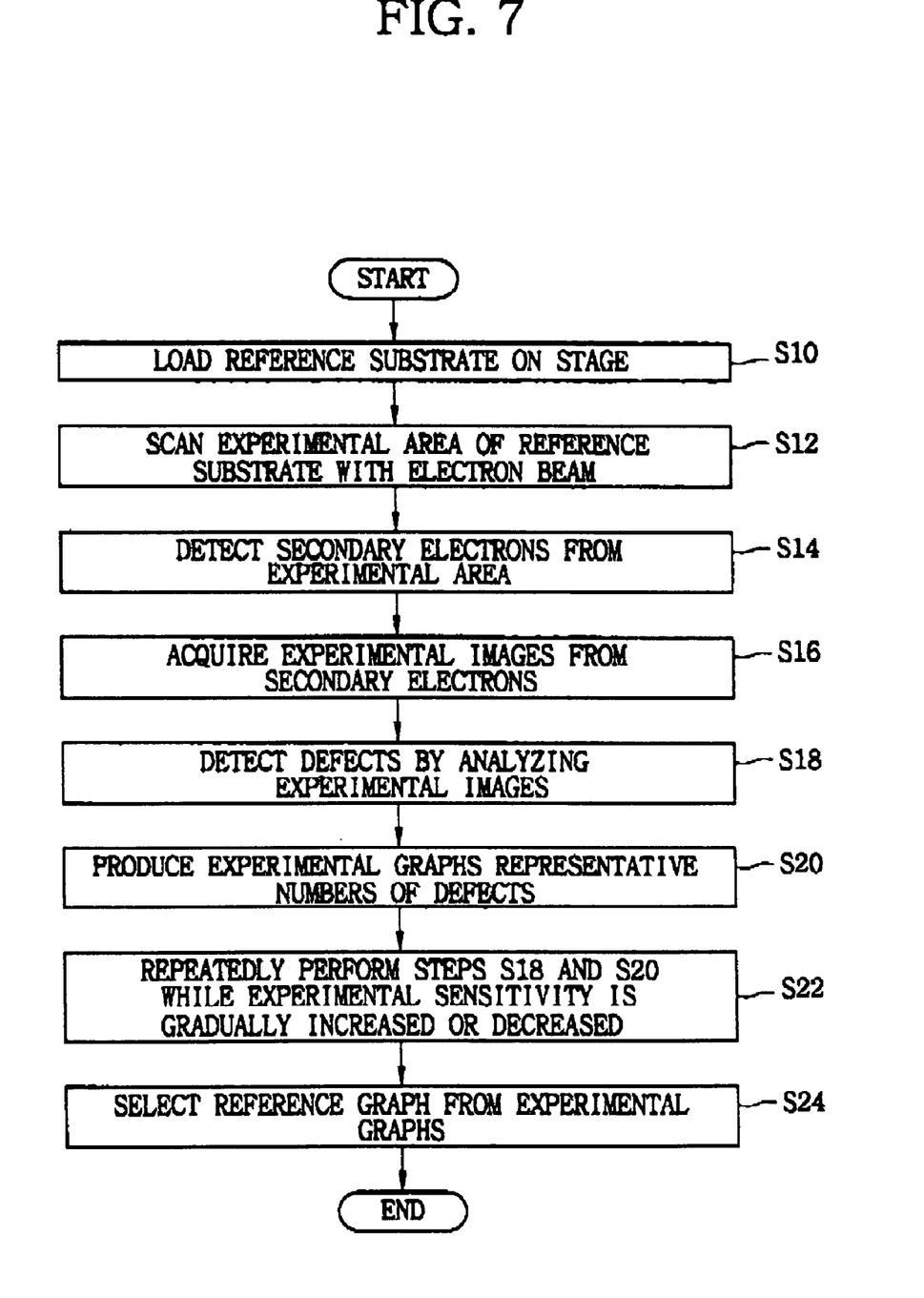
FIG. 7 is an example flow chart illustrating a method of producing a reference graph from an experimental area on a reference substrate.
Figure 8:
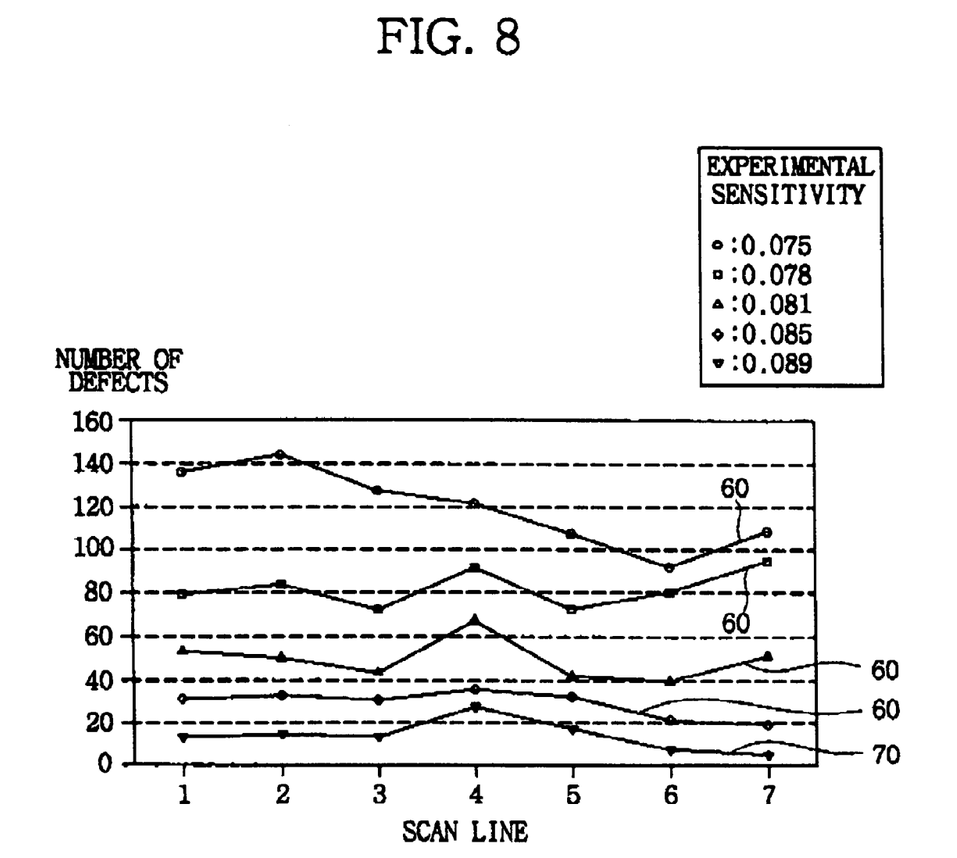
FIG. 8 is an example reference graph and experimental graphs indicating the number of defects detected in the experimental area of the reference substrate.

FIG. 7 is a flow chart illustrating a method of producing a reference graph from an experimental area on a reference substrate and FIG. 8 is the reference graph and experimental graphs indicating the number of defects detected in the experimental area of the reference substrate. A method in accordance with example embodiments for acquiring the reference graph will be described with reference to FIGS. 7 and 8.

In step S10, the reference substrate is loaded on the stage 140. The driving unit 142 adjusts the position of the stage 140 such that the electron beam 20 is irradiated onto the experimental area of the reference substrate. In step S12, the electron beam 20 scans the experimental area of the reference substrate. The experimental area includes a plurality of scan lines. The electron beam 20 transmitted through the column 114 sequentially scans the scan lines of the experimental area.

In step S14, secondary electrons emitted from the experimental area are detected. The secondary electrons emitted along the scan lines of the experimental area are detected by the detector 144 to which the bias voltage is applied. The detector 144 converts the current signal corresponding to detected secondary electrons into the voltage signal and amplifies the voltage signal. In step S16, the experimental images are acquired from the detected secondary electrons. The voltage signal amplified by the detector 144 are converted into digital image data of the experimental images corresponding to the scan lines of the experimental area by the image acquisition unit 146.

In step S18, the defects are detected by analyzing the experimental images. The image processing unit 148 analyzes the experimental images using the experimental sensitivity and then detects the defects on the experimental area by scan lines of the experimental area.

In step S20, the experimental graph 60, which represents the number of defects, is produced. The graphic unit 150 produces the experimental graph 60 showing the number of defects corresponding to the scan lines of the experimental area. In step S22, the steps S18 and S20 are repeatedly performed while the experimental sensitivity is gradually increased or decreased. In step S24, the reference graph 70 is selected from the produced experimental graphs 60. One of the experimental graphs 60 corresponding to the actual number of the defects on the experimental area may be selected for the reference graph 70. The experimental graphs 60 may be produced by repeatedly performing the steps S10 to S20 while the experimental sensitivity is gradually increased or decreased.

The display unit 158 displays the experimental graphs 60, the reference graph 70, and the inspection graph 50. The worker (i.e. a user) may adjust the initial sensitivity in accordance with the sensitivity difference corresponding to the difference between the inspection graph 50 and the reference graph 60. Accordingly, the time required for performing the operation state testing process on the electron beam inspection apparatus may be decreased.

As mentioned above, the method for testing the operation state of the electron beam inspection apparatus may be completed by manually adjusting the initial sensitivity using the inspection graph and the reference graph. However, the method for testing the operation state of the electron beam inspection apparatus may be performed automatically.

Figure 9:
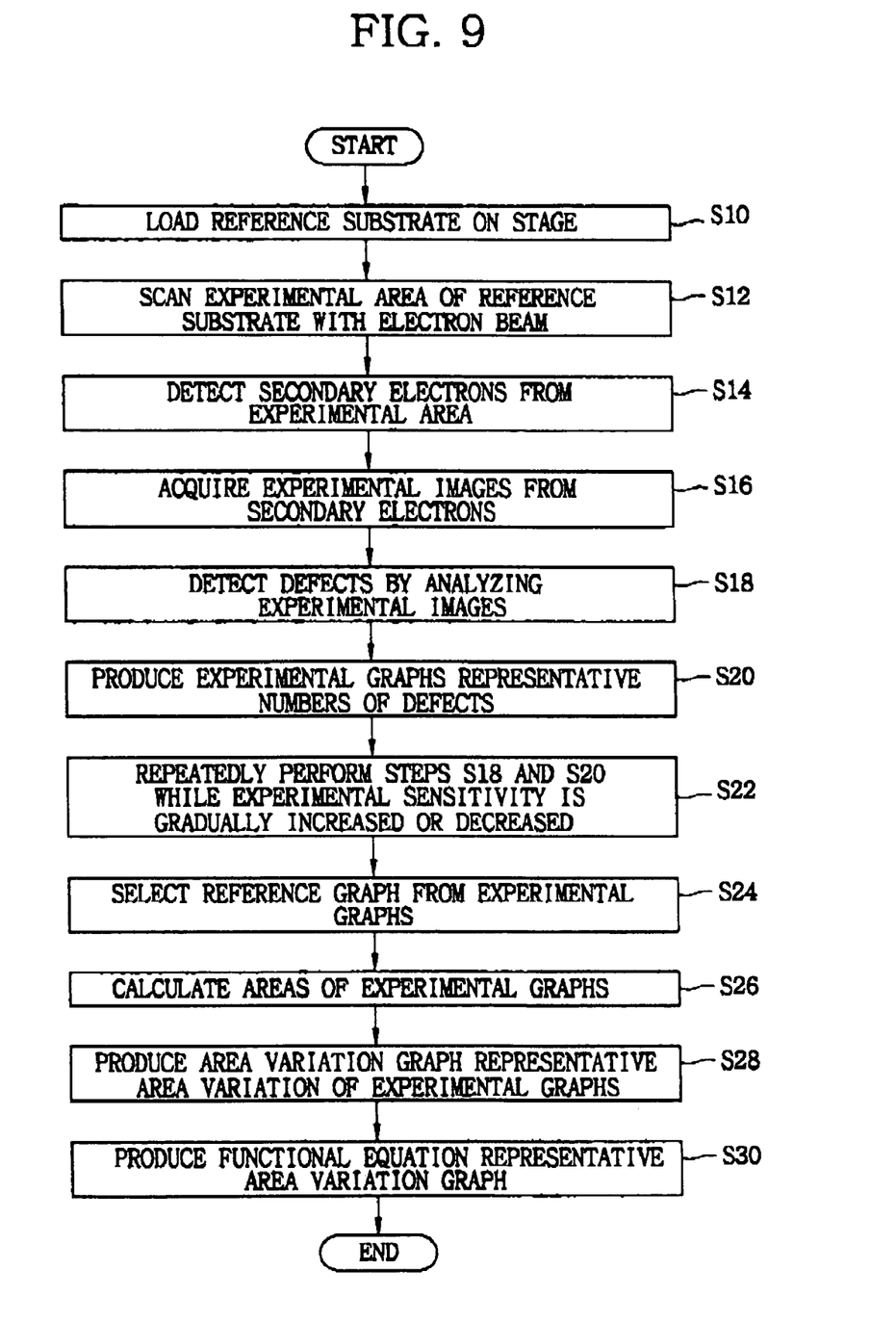
FIG. 9 is an example flow chart illustrating a method of producing an area variation graph from an experimental area of a reference substrate.
Figure 10:
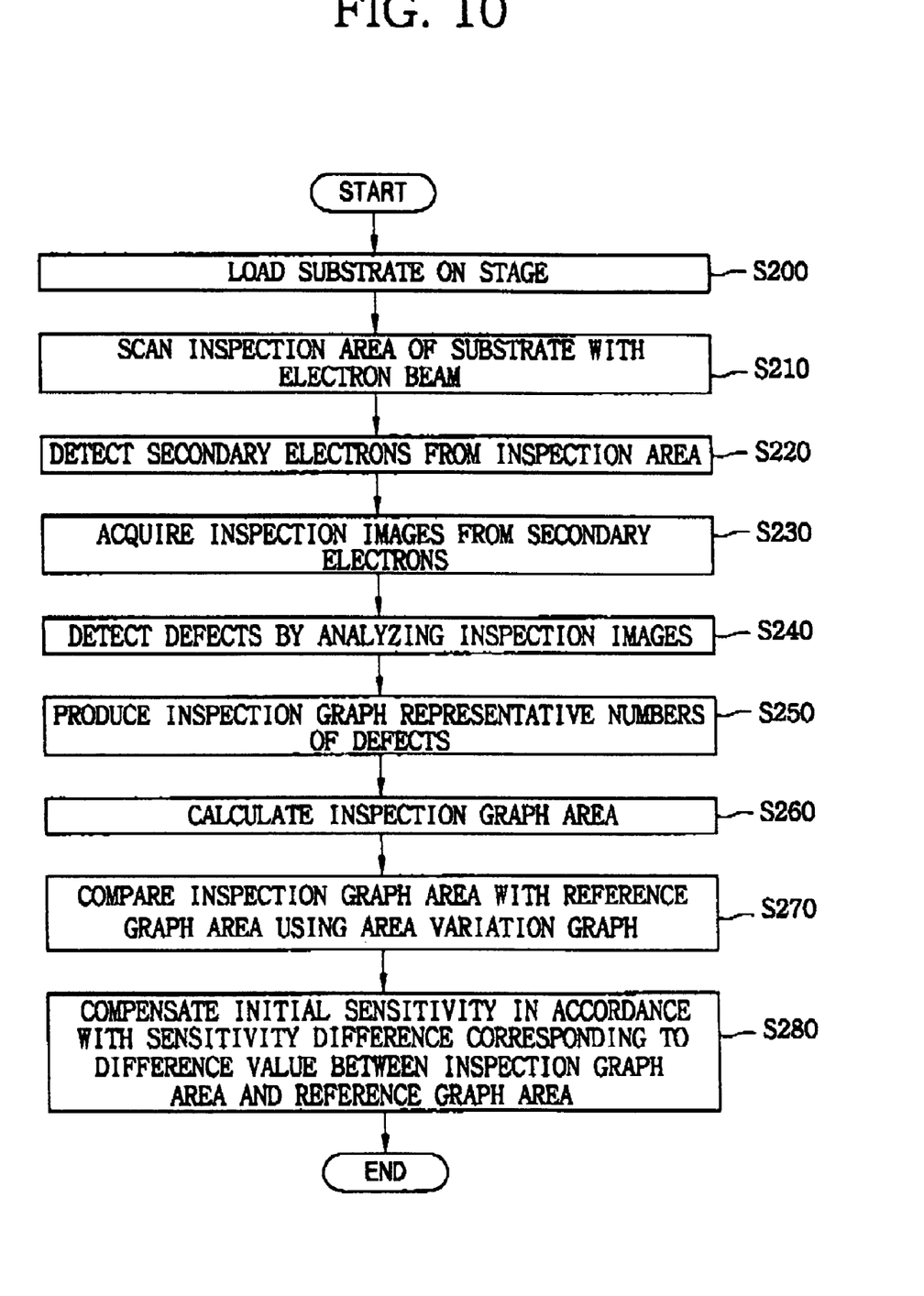
FIG. 10 is an example flow chart illustrating a method of testing an operation state of an electron beam inspection apparatus using an area variation graph.
Figure 11:
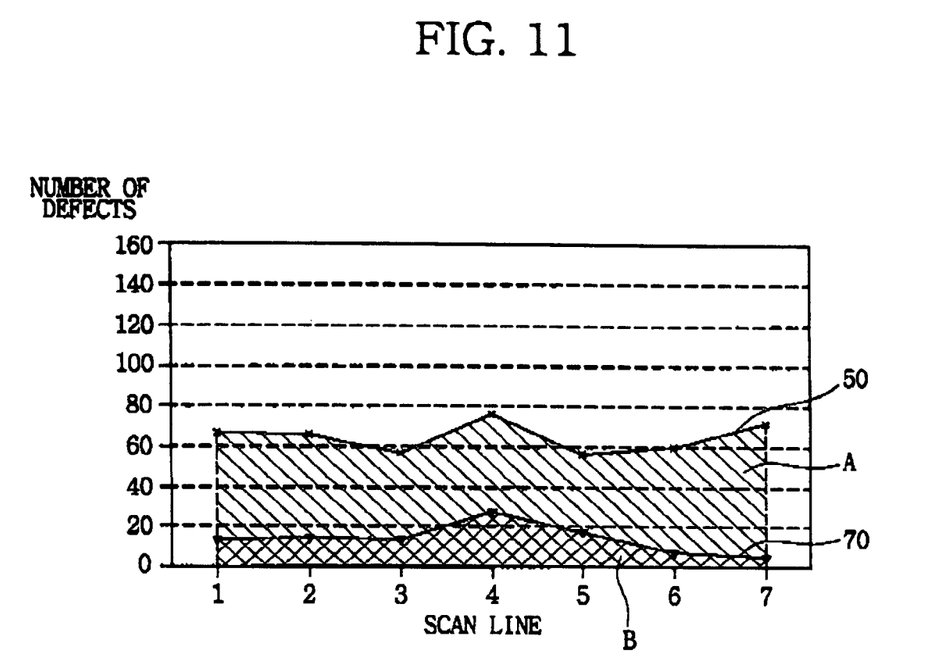
FIG. 11 is an example graph showing an inspection graph area and a reference graph area.
Figure 12:
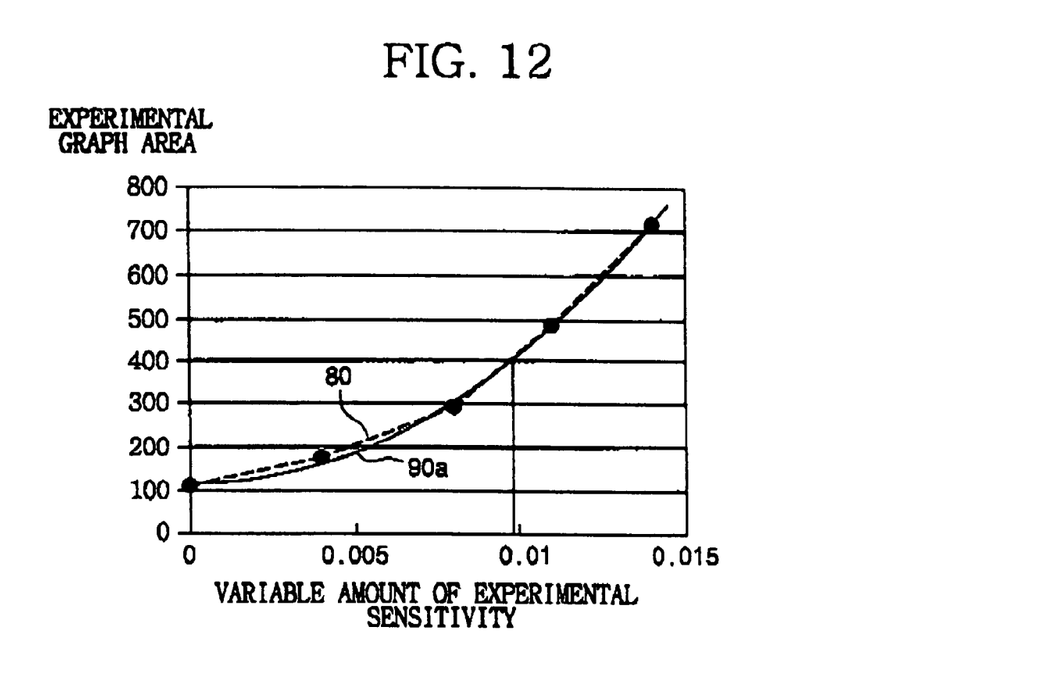
FIG. 12 is an example graph illustrating a functional equation obtained from an area variation graph.
Figure 13:
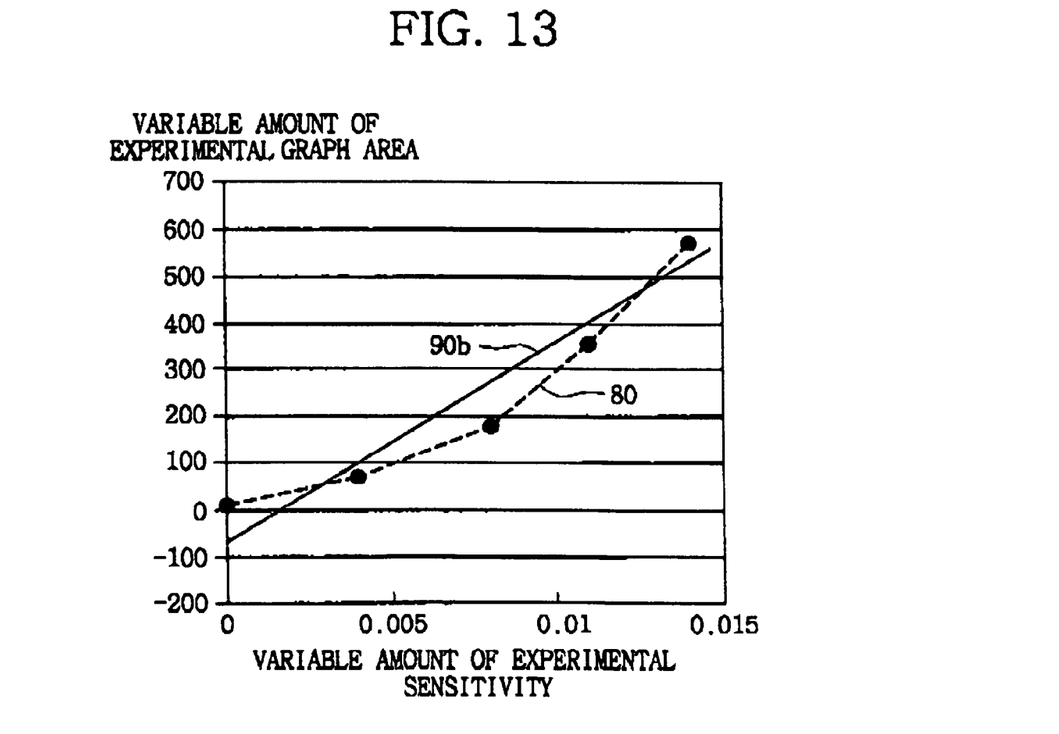
FIG. 13 is an example graph illustrating a functional equation obtained from an area variation graph.

FIG. 9 is an example flow chart illustrating a method of producing an area variation graph from the experimental area of the reference substrate. FIG. 10 is an example flow chart illustrating a method of testing the operation state of the electron beam inspection apparatus using the area variation graph. FIG. 11 is an example graph showing an inspection graph area and a reference graph area. FIG. 12 is an example graph illustrating one example of a functional equation obtained from the area variation graph. FIG. 13 is an example graph illustrating another example of the functional equation obtained from the area variation graph.

In FIG. 9, detailed descriptions of steps S10 to S24 will be omitted since these steps are similar to those already described in connection with the method for acquiring the reference graph shown in FIG. 7. In step S26, the areas of the experimental graphs 60 and the reference graph area are calculated. The operation unit 152 calculates the areas of the experimental graphs 60 including the reference graph 70. The memory unit 156 stores the areas of the experimental graphs 60.

In step S28, the area variation graph 80, indicating the area variation of the experimental graphs 60, is produced. The operation unit 152 produces the area variation graph 80, indicating the area variation of the experimental graphs 60 in accordance with a variable amount of the experimental sensitivity. The area variation graph 80 may be produced from a relationship between the areas of the experimental graphs 60 and a variable amount of the experimental sensitivity. Further, the area variation graph 80 may be produced from a relationship between a variable amount of the area of the experimental graph 60 and the variable amount of the experimental sensitivity.

In step S30, the functional equation is produced from the area variation graph 80. The functional equation is produced by the operation unit 152 and may be a simple equation 90b or a quadratic equation 90a.

In FIG. 10, steps S200 to S250 are similar to those already described in connection with the method for testing the operation state of the electron beam inspection apparatus shown in FIG. 2, thus detailed descriptions of the steps S200 to S250 are omitted. In step S260, inspection graph area (A) is calculated. Alternatively, the inspection graph area (A) may be calculated by the operation unit 152.

In step S270, the inspection graph area (A) and reference graph area (B) are compared to each other using the area variation graph 80. The operation unit 152 compares the inspection graph area (A) with the reference graph area (B) using the area variation graph and calculates the sensitivity difference corresponding to the difference in value between the inspection graph area (A) and the reference graph area (B).

In step S280, the initial sensitivity is compensated in accordance with the sensitivity difference corresponding to the difference in value between the inspection graph area (A) and the reference graph area (B). The compensator 154 adjusts the initial sensitivity in accordance with the sensitivity difference to restore the electron beam inspection apparatus 100 to a normal operation state.

In embodiments, the operation unit 152 may produce a different value that is between the inspection graph area (A) and the reference graph area (B) using the functional equation graph 80, representing the area variation.

Table 1 shows the area variation of the experimental graphs in accordance with the variable amount of the experimental sensitivity.

TABLE 1

| Experimental sensitivity | 0.089 | 0.085 | 0.081 | 0.078 | 0.075 |
|---|---|---|---|---|---|
| Variable amount of experimental sensitivity | 0 | 0.004 | 0.008 | 0.011 | 0.014 |
| Experimental graph area | 110.5 | 175 | 293 | 485.5 | 713 |
| Variable amount of experimental graph area | 0 | 64.5 | 182.5 | 375 | 602.5 |

Referring to Table 1 and FIG. 12, the area variation graph 80 may be expressed with the quadratic equation (90a) as follows:

$$y=3\times10^6 x^2 - 842.86x + 115.05 \quad (90a)$$

where, y is the area of the experimental graph 60, and x is the variable amount of experimental sensitivity.

For example, when the reference graph area (B) is 110.5, and the inspection graph area (A) is 400, the sensitivity difference is approximately 0.01. Here, the operation unit 152 calculates the sensitivity difference using the quadratic equation (90a), and the compensator 154 adjusts the initial sensitivity in accordance with the calculated sensitivity difference. That is, the compensator 154 adjusts the initial sensitivity to be loose by about 0.01.

Referring to FIG. 13, the area variation graph 80 may be also expressed with the simple equation (e.g. a linear equation) (90b) as follows:

$$y=42343x - 68.441 \quad (90b)$$

where, y is the variable amount of the experimental graph area, and x is the variable amount of experimental sensitivity.

As mentioned above, though performed using the area variation graph and the functional equation (90a or 90b) produced from the reference substrate, the method for testing the operation state of the electron beam inspection apparatus may be performed using an area variation graph and a functional equation produced from a substrate on which various patterns or layers are formed.

According to embodiments of the present invention, the initial sensitivity may be compensated in accordance with the sensitivity difference corresponding to the difference in value between the inspection graph area and the reference graph area. The sensitivity difference may be readily calculated by means of the area variation graph or the functional equation.

Accordingly, there may be no need to repeatedly perform the operation state testing process of the electron beam inspection apparatus in order to adjust the electric field and the magnetic field of the magnetic lens, thereby decreasing the time required for the operation state testing process. Further, throughput of the electron beam inspection apparatus may be increased.

In the drawings and specification of the present invention, there have been disclosed embodiments of the invention, and although specific terms are employed, they are used in a generic and descriptive sense only and not for purposes of limitation, the scope of the invention being set forth in the following claims.

What is claimed is:

1. A method which tests an operation state of an electron beam inspection apparatus, comprising:
    scanning at least one scan line on a predetermined inspection area of a substrate with an electron beam and detecting secondary electrons emitted from the at least one scan line;
    generating at least one inspection image corresponding to the at least one scan line from the detected secondary electrons;
    analyzing the at least one inspection image using an initial sensitivity and generating an inspection graph indicating the detected number of defects on the at least one scan line; and
    comparing the inspection graph with a reference graph to determine if the initial sensitivity needs to be adjusted.

2. The method of claim 1, wherein the defects are detected by comparing gray levels of pixels of the at least one inspection image.

3. The method of claim 1, wherein the reference graph is produced by analyzing reference images acquired from a reference substrate using a reference sensitivity.

4. The method of claim 3, wherein the initial sensitivity is substantially the same as the reference sensitivity.

5. The method of claim 1, further comprising adjusting the initial sensitivity so that a difference between the inspection graph and the reference graph is within a predetermined tolerance range when the difference between the inspection graph and the reference graph exceeds the tolerance range.

6. The method of claim 1, further comprising displaying the inspection graph and the reference graph.

7. The method of claim 1, wherein the reference graph is generated by:
    scanning at least one scan line on a predetermined experimental area on a reference substrate using an electron beam and detecting secondary electrons emitted from the at least one scan line at the experimental area;
    generating at least one experimental image from the detected secondary electrons emitted from the experimental area;
    analyzing the at least one experimental image and generating a plurality of experimental graphs having different experimental sensitivities, wherein each of the plurality of experimental graphs indicate a detected number of defects on the at least one scan line in the experimental area; and
    selecting the reference graph from the plurality of experimental graphs.

8. The method of claim 7, wherein an inspection graph area of the inspection graph is compared with a reference graph area of the reference graph.

9. The system of claim 7, further comprising calculating areas of the plurality of experimental graphs and producing an area variation graph from an area variation of the experimental graphs.

10. The method of claim 9, wherein the comparing the inspection graph with the reference graph comprises:
    calculating an inspection graph area; and
    comparing the inspection graph area with a reference graph area using the area variation graph.

11. The method of claim 10, further comprising adjusting the initial sensitivity according to a sensitivity difference which is a difference in value between the inspection graph area and the reference graph area.

12. The method of claim 10, further comprising:
    producing a functional equation representative of the area variation graph;
    calculating a sensitivity difference corresponding to a difference value between the inspection graph area and the reference graph area using the functional equation; and adjusting the initial sensitivity in accordance with the sensitivity difference.

13. The method of claim 12, wherein the functional equation is a simple equation or a quadratic equation.

14. A method which tests an operation state of an electron beam inspection apparatus, comprising:
scanning at least one scan line on a predetermined inspection area of a substrate with an electron beam and detecting secondary electrons emitted from the at least one scan line;
generating at least one inspection image corresponding to the at least one scan line from the detected secondary electrons;
comparing gray levels of pixels of the at least one inspection image using an initial sensitivity to detect defects on the at least one scan line;
generating an inspection graph representing the number of the detected defects on the at least one scan line; and
comparing the inspection graph with a reference graph and adjusting the initial sensitivity to compensate for a difference between the inspection graph and the reference graph.

15. The method of claim 14, wherein the reference graph is generated by:
scanning at least one scan lines on a predetermined experimental area on a reference substrate using an electron beam and detecting secondary electrons emitted from the at least one scan line at the experimental area;
generating at least one experimental image from the detected secondary electrons emitted from the experimental area;
analyzing the at least one experimental image and generating a plurality of experimental graphs having different experimental sensitivities, wherein each of the plurality of experimental graphs indicate a detected number of defects on the at least one scan line in the experimental area; and
selecting the reference graph from the plurality of experimental graphs.

16. The method of claim 15, wherein an inspection graph area of the inspection graph is compared with a reference graph area of the reference graph.

17. The method of claim 15, further comprising calculating areas of the plurality of experimental graphs and producing an area variation graph from the areas of the experimental graphs.

18. The method of claim 17, wherein comparing the inspection graph with the reference graph comprises:
calculating an inspection graph area; and
comparing the inspection graph area with a reference graph area using the area variation graph.

19. The method of claim 18, wherein the initial sensitivity is adjusted according to a sensitivity difference which is a difference in value between the inspection graph area and the reference graph area.

20. The method of claim 18, further comprising:
producing a functional equation representing the area variation graph; and
calculating a sensitivity difference corresponding to a difference in value between the inspection graph area and the reference graph area using the functional equation, wherein the initial sensitivity is adjusted in accordance with the sensitivity difference.

21. The method of claim 20, wherein the functional equation is a simple equation or a quadratic equation.

22. An electron beam inspection apparatus, comprising:
an electron beam source which generates an electron beam and controls an advancing direction of the electron beam so that the electron beam scans at least one scan line in a predetermined inspection area on a substrate;
a stage which supports the substrate;
a driving unit which adjusts a position of the stage such that the electron beam is irradiated onto a surface of the inspection area;
a detector which detects secondary electrons emitted from the at least one scan line;
an image acquisition unit connected to the detector which generates at least one inspection image corresponding to the at least one scan line from the detected secondary electrons;
an image processing unit which analyzes the at least one inspection image using an initial sensitivity to detect defects on the at least one scan line;
a graphic unit which produces an inspection graph indicating the number of the detected defects on the at least one scan line: and
an operation unit which compares the inspection graph with a reference graph.

23. The apparatus of claim 22, further comprising a compensator which compensates the initial sensitivity according to a difference between the inspection graph and the reference graph.

24. The apparatus of claim 22, wherein the reference graph is selected from one of a plurality of experimental graphs which each represent a number of defects detected from a predetermined experimental area on a reference substrate, wherein each of the plurality of experimental graphs uses a different experimental sensitivity.

25. The apparatus of claim 24, wherein the operation unit comprises:
a first operator which calculates areas of the experimental graphs, a reference graph area and an inspection graph area;
a comparator which compares the inspection graph area with the reference graph area; and
a second operator which determines a sensitivity difference, which is a difference in value between the inspection graph area and the reference graph area.

26. The apparatus of claim 25, wherein the operation unit further comprises a third operator which produces an area variation graph representing an area variation of the experimental graphs in accordance with a variable amount of the experimental sensitivity, a functional equation representing the area variation graph, and a sensitivity difference corresponding to a difference value between the inspection graph area and the reference graph area.

27. The apparatus of claim 25, further comprising a compensator which compensates the initial sensitivity according to a sensitivity difference which is a difference in value between the inspection graph area and the reference graph area.

28. The apparatus of claim 25, further comprising a memory unit which stores the experimental graphs, the reference graph, the area variation graph, and the inspection graph.

29. The apparatus of claim 22, further comprising a display unit which displays the inspection graph and the reference graph.

* * * * *